(12) United States Patent
Scott (10) Patent No.: US 7,785,104 B2
(45) Date of Patent: Aug. 31, 2010

(54) ACCELERATED ORTHODONTIC APPARATUS AND METHOD

(76) Inventor: Michael Glenn Scott, 242 Maili Ct., Windsor, CA (US) 95492

( * ) Notice: Subject to any disclaimer, the term of this patent is extended or adjusted under 35 U.S.C. 154(b) by 120 days.

(21) Appl. No.: 12/001,928

(22) Filed: Dec. 12, 2007

(65) Prior Publication Data
US 2008/0102415 A1 May 1, 2008

Related U.S. Application Data

(62) Division of application No. 11/189,628, filed on Jul. 25, 2005, now Pat. No. 7,329,122.

(51) Int. Cl.
*A61C 3/00* (2006.01)
(52) U.S. Cl. .......................... 433/75; 606/96
(58) Field of Classification Search .............. 433/5, 433/6, 18, 24, 215, 75; 606/96
See application file for complete search history.

(56) References Cited

U.S. PATENT DOCUMENTS 5,306,278 A * 4/1994 Dahl et al. ............... 606/96
7,097,451 B2 * 8/2006 Tang ...................... 433/76

OTHER PUBLICATIONS

Wikipedia contributors, "Dentures" Wikipedia, The Free Encyclopedia, http://en.wikipedia.org/wiki/Dentures (last modified Dec. 11, 2009). p. 3.

Ralph Lewis, "Interview Summary", USPTO, Alexandria VA (May 8, 2006) p. 1.
Dr. Robert L. Crosby, "Fracture of Buccal Cortical Plate: What To Expect?", OsseoNews, http://www.osseonews.com/fracture-of-buccal-cortical-plate-what-to-expect/ (Jun. 13, 2007) p. 4.
Brian K., "Hospital Needs to Color Code Surgical Instruments", Finishing Dot Com, http://www.finishing.com/324/06.shtml, (Aug. 3, 2009) p. 1.

* cited by examiner

*Primary Examiner*—Cris L Rodriguez
*Assistant Examiner*—Eric Rosen
(74) *Attorney, Agent, or Firm*—Joseph E. Schoenholtz (57) ABSTRACT

An apparatus and method for patients requiring repositioning of misaligned teeth who typically undergo orthodontic treatment to move the teeth into corrected positions. The orthodontic methods typically require lengthy procedures involving the application of light forces to the teeth to effect movement as accomplished by braces or other appliances. The apparatus and method includes the administration of a needle corticotomy to select regions that have been identified as absent any landmarks to avoid. The method is accomplished without the use of freeze-dried and bovine bone and without a mucoperiosteal flap procedure, resulting in low medical risk and providing a simplified and less time consuming procedure as compared to the prior art, and furthermore wherein the method effects a significant reduction in the time required to complete an orthodontic case while also significantly reducing the discomfort and recovery time for the patient.

6 Claims, 3 Drawing Sheets

ACCELERATED ORTHODONTIC APPARATUS AND METHOD

This patent application claims the benefit of priority of prior Provisional Patent Application Ser. No. 60/522,996, filed in the United States Patent and Trademark Office on Nov. 30, 2004.

FIELD OF THE INVENTION

The present invention relates to an apparatus and method for performing dental procedures associated with orthodontics and, more particularly, to a method of performing orthodontic procedures in an accelerated fashion and to apparatus useful in performing those procedures.

Orthodontics is a branch of dentistry dealing with misaligned teeth and their correction, typically by means of braces, aligners or similar appliances. In many orthodontic cases tooth positioning or straightening is accomplished by means of administering light force to the tooth for a period of time until the tooth root moves within the jaw and is repositioned. The tooth root is embedded in a relatively soft and highly vascular bone in the middle of the jawbone, known as medullary bone. Both the maxilla or upper jawbone and the mandible or lower jawbone are comprised of medullary bone surrounded by a hard exterior bone structure known as the cortical plate of bone. The tooth is held firmly in position by the cortical plate. Generally, by placing a light and persistent force on a tooth for purposes of repositioning or moving the tooth relative to the maxilla or mandible, the cortical plate responds as if an injury to the bone has occurred by softening slightly to ease the force on the tooth allowing the tooth to move thereby effecting the tooth repositioning. The softened cortical plate hardens again once the force subsides. The hardening is indicative of healing.

This osteogenic process, wherein the bone softens and hardens, is an essential element of orthodontics. By administering a series of incremental calculated forces to the tooth, the tooth position may be gradually adjusted over a period of time.

Typically, in order to reposition misaligned teeth, the dentist will apply a series of light forces to the teeth by means of braces, wires, forms or other mechanical devices that are periodically readjusted after the tooth (or teeth) repositions in the now softened cortical plate. The device is incrementally readjusted to apply a new light force to continue the movement of the tooth until the tooth moves to the desired position. Once the light force is removed, the cortical plate hardens and secures the tooth in the new position. The principal disadvantage is that it takes many months, even years, to accomplish this slow osteogenic process sufficient to move the tooth or teeth into their desired positions.

As known to those skilled in the art, osteogenesis is induced by persistent light force being applied to the tooth resulting in softening of the cortical plate, thereby permitting the tooth to move. Additionally, it is known that when an additional injury is purposefully inflicted to the cortical plate, such as the drilling or puncturing of a small hole through the plate, the cortical plate softens around the injury.

Corticotomy is the process of intentionally inducing injury to the cortical plate for the purpose of softening the cortical plate. A penetration of the cortical plate permits vascular access from the medullary bone to the now exposed portions of the cortical plate thereby facilitating rapid osteogenic repair of the injury site.

The softening of the cortical plate in an area surrounding the injury site results in a process known as regional acceleratory phenomenon (RAP). Therefore, it is known according to prior art taught by Kole, Suya and later Wilcko to utilize multiple corticotomies (injuries inflicted to the cortical plate) in conjunction with traditional orthodontic techniques (to urge motion of the tooth or teeth proximate the softened cortical plate) to accelerate the repositioning of teeth.

In essence, RAP permits more rapid repositioning of the tooth or teeth by conventional orthodontic devices than would otherwise be possible. As no one likes to wear orthodontic devices intended to move the tooth or teeth, there is strong demand to accomplish the repositioning as quickly as possible.

Wilcko, in U.S. Pat. No. 6,109,916, described a method wherein multiple corticotomies are administered to soften sections of the cortical plate in the region of the desired tooth movement for the purposes of softening the cortical plate to a greater extent than what is achieved by applying only light forces from a mechanical appliance. The increased softening of the cortical plate results in an accelerated movement of the tooth through the cortical plate and in the underlying medullary bone thereby significantly reducing the overall time required to reposition the tooth to the desired position.

However, a significant, principle disadvantage of the prior art is the required step of removing the gum or gingivae from the cortical plate in order to gain access to the bone surface. As is described in greater detail hereinafter, removal of the gingivae from the cortical plate exposes the cortical plate to view, thereby permitting improved accuracy of the placement and application of the corticotomy (injury to the cortical plate). An improvement in accuracy is important to minimize the potential for damage to underlying nerves, vessels, and other sensitive structures, also known as "landmarks", and which are described in greater detail hereinafter.

The method to accomplish surgical removal of the gingivae is a mucoperiosteal full flap procedure necessitating incisions into the gum to separate the gum from the jaw bone (i.e., from the teeth and cortical plate). Once the gingivae are lifted away from the bone, the cortical plate is exposed. The practitioner can now see sufficient variation in the surface features of cortical plate to suggest some of the locations of the critical landmarks that are to be avoided. The corticotomy is then performed by penetrating or otherwise damaging the cortical plate while avoiding the landmarks. Even so, there is risk that certain important landmarks may be missed by visual examination.

Then, as is further described by Wilcko, a solution of freeze-dried bone and bovine bone is applied to the surface of the cortical plate and finally the mucoperiosteal flap is sutured back into position.

The mucoperiosteal full flap procedure inevitably causes considerable trauma and damage to the gingivae. This trauma and damage substantially increase the time for healing to occur. Raising of the mucoperiosteal flap also tears the bonds that adhere the gingivae to the cortical plate, the reconnection thereof taking additional time to heal.

Furthermore, there is risk that the gingivae may not bind as tightly to the teeth after the mucoperiosteal flap procedure as they were bonded before it occurred. This can cause discomfort for the patient from food being wedged under the gums after the mucoperiosteal flap procedure that would not have occurred prior to the procedure. An inadequate bond to the tooth can promote the growth of bacteria and cause, at a minimum, halitosis. It can also lead to an increase risk of eventually developing periodontal disease and possible eventual tooth loss.

After the mucoperiosteal procedure and corticotomy is complete, considerable trauma has been experienced by the gingivae and, accordingly, the patient is quite uncomfortable. The patient typically must take considerable pain medication (usually analgesics) to reduce the substantial physical discomfort that he or she is experiencing, often for several days, after such a procedure has been performed.

Similarly, there in an increased chance for infection to occur that is generally proportional to the damage that has been inflicted to the gingivae. The use of antibiotics are often also administered to help reduce this risk.

In addition, the use of dried bone or bovine bone includes the addition of a foreign body into the mouth of the patient and such inclusion incurs an additional risk of infection and possibly even rejection by the immune system. The foreign body may also add to irritation and general discomfort.

Nevertheless, to generate sufficient RAP (regional acceleratory phenomenon) it is believed that a mucoperiosteal flap procedure must be performed to permit viewing of the cortical plate prior to and during the corticotomy. The mucoperiosteal flap procedure must, according to prior art, be accomplished proximate each of the teeth that are to be repositioned.

Knowledge of the location of the important underlying landmarks is essential in order to avoid damage to those features. The prior art teaches the use of the mucoperiosteal flap procedure as necessary to reveal the surface of cortical plate prior to effecting the required corticotomy.

Another disadvantage inherent with the above-described prior art procedure is that, although the resultant view of the cortical plate surface from the mucoperiosteal flap procedure provides improved visualization of the landmark locations and an understanding of the general anatomy of the region, there are important landmarks which remain undetermined. Consequently, the medical risk is reduced by the mucoperiosteal flap procedure, but not eliminated.

Despite full visibility of the cortical plate with the mucogingival flap used in the prior art, landmarks peculiar to a specific patient (i.e., anomalies) may not be fully visible.

Damage to certain landmarks can cause infection, loss of sensation, and other potentially serious and irreversible problems. Such damage is a liability risk for the practitioner and that increased liability is ultimately expressed through higher liability insurance premiums that are passed on from the practitioner as increased cost to the patient associated with any corticotomy that is intended to promote RAP, and therefore to allow for the more rapid repositioning of the tooth or teeth.

It also takes time for the dental practitioner to perform the mucoperiosteal flap procedure, and this time also contributes to increased cost for the patient. It also increases the time the patient must sit in the dental chair and endure a generally unpleasant procedure. After the corticotomy is complete, there is also an increased amount of time required to suture the gingivae. Again, this added cost and related discomfort are passed on to the patient to bear.

As mentioned above, while any injury to the cortical plate may induce a softening of the plate, to optimally induce RAP it has been found by the inventor herein that the cortical plate must be penetrated an amount sufficient to pass into a vascular area of the medullary bone and cause bleeding. The resultant bleeding through the cortical plate that a prior-art practitioner observes during corticotomy and after having performed the mucoperiosteal flap procedure would similarly be coming from a vascular area of the medullary bone, although a prior art practitioner would be hesitant to drill that deep less inadvertent contact with a landmark occur. The mucoperiosteal flap procedure was therefore necessary in order to verify that sufficient damage to the cortical plate had been accomplished (either a general roughening of the surface of the plate or, if the practitioner drilled deeper into the medullary bone to ensure that penetration into the vascular area of the medullary bone had occurred). To make such determination either way the cortical plate had to be made visible and therefore the mucoperiosteal flap procedure had to first be performed. Otherwise, the practitioner would not know if the bleeding was coming from a vascular region of the medullary bone or from the gingivae.

Therefore, there exists a need for an improved apparatus and method for performing a corticotomy to generate RAP sufficient to facilitate accelerated orthodontic procedures while decreasing the negative effects associated with a mucoperiosteal flap procedure.

Clearly, such an apparatus and method would be useful and desirable.

DESCRIPTION OF PRIOR ART

Orthodontics, is, in general, known. Corticotomies are also known, as the following patent describes:

U.S. Pat. No. 6,109,916 to Wilcko, et al, that issued Aug. 29, 2000.

While the structural arrangements of the above described apparatus and method may, at first appearance, have similarities with the present invention, it differs in material respects. These differences, which will be described in more detail hereinafter, are essential for the effective use of the invention and which admit of the advantages that are not available with the prior art.

OBJECTS AND SUMMARY OF THE INVENTION

It is an object of the present invention to significantly reduce the expense required for a corticotomy assisted type of orthodontic procedure.

Another object of the invention is to reduce the risk of infection to a patient following a corticotomy.

Still another object of the invention is to decrease the length of time for recovery following a corticotomy.

Still yet another object of the invention is to eliminate the need for even a partial mucoperiosteal flap surgery procedure in order to perform a corticotomy.

Yet another important object of the invention is to eliminate the need for a mucoperiosteal full flap surgery procedure in order to perform a corticotomy.

Still yet another important object of the invention is to reduce the risk of medical complications or other adverse effects arising to a patient following a corticotomy.

A first continuing object of the invention is to reduce the time that is actually required for a dentist to perform a corticotomy assisted orthodontic procedure.

A second continuing object of the invention is to reduce the duration of time that a patient must actually endure (sit in the dentist's chair) in order to perform a corticotomy assisted orthodontic procedure.

A third continuing object of the invention is to eliminate the need for the placement of bone grafting material adjacent to the cortical plate proximate the areas of injury to the plate associated with a corticotomy.

A fourth continuing object of the invention is to reduce the discomfort that a patient experiences during a corticotomy assisted orthodontic procedure.

A fifth continuing object of the invention is to reduce the level of discomfort that a patient experiences after having had a corticotomy assisted orthodontic procedure.

A sixth continuing object of the invention is to allow a dentist to perform a corticotomy without removal of the gingivae from the jawbone.

A seventh continuing object of the invention is to facilitate the location of landmarks prior to a corticotomy.

An eighth continuing object of the invention is to provide an apparatus that is useful in avoiding landmarks during corticotomy.

A ninth continuing object of the invention is to provide a method that determines the location of landmarks to avoid during corticotomy.

A tenth continuing object of the invention is to provide a method for performing corticotomy by drilling directly through the gingivae.

An eleventh continuing object of the invention is to provide a template that is placed over at least a portion of the teeth and gingivae that is useful in avoiding landmarks during corticotomy.

A twelfth continuing object of the invention is to provide a method that uses a CTscan (also sometimes referred to as a "CAT scan" or as a "CT scan") to create a file of at least a portion of the jawbone of a patient in need of orthodontic treatment, and wherein the file includes an indication of any possible landmarks to avoid contacting during corticotomy.

A thirteenth continuing object of the invention is to provide a method that uses a CTscan to create a file of at least a portion of the jawbone of a patient in need of orthodontic treatment and wherein the file can be used to create a virtual image of the portion of the jawbone.

A fourteenth continuing object of the invention is to provide a method that uses a CTscan to create a file of at least a portion of the jawbone of a patient in need of orthodontic treatment and wherein that file can be used to provide indication as to where to drill through the gingivae and avoid landmarks.

A fifteenth continuing object of the invention is to provide a method for x-raying at least a portion of a jawbone of a user prior to corticotomy, and of using the data acquired to avoid landmarks.

A sixteenth continuing object of the invention is to provide a method for x-raying at least a portion of a jawbone of a user prior to corticotomy, and of using the data acquired to provide indication during the corticotomy where a dentist can drill through the gingivae and through the cortical plate and into the medullary bone underneath while avoiding landmarks.

A seventeenth continuing object of the invention is to provide a method and apparatus for indicating where a dentist may drill through the gingivae and through the cortical plate and which also indicates the depth of drilling that is desired.

An eighteenth continuing object of the invention is to provide a method and apparatus for x-raying at least a portion of a jawbone of a user prior to corticotomy, and of using the data acquired (image file) to provide indication during the corticotomy where a dentist can drill through the gingivae and through the cortical plate and how deep into the medullary bone the drill may pass sufficient to draw blood and begin RAP while avoiding certain landmarks.

A nineteenth continuing object of the invention is to provide an apparatus that regulates the depth of drilling at each bore site through the gingivae and through the cortical plate to a depth that is preferred at each location.

A twentieth continuing object of the invention is to provide an apparatus and method that ensures that when drilling through the gingivae and into the cortical plate the penetrations are made only in the interproximal regions between the roots of two adjacent teeth.

A twenty-first continuing object of the invention is to provide an apparatus and method that permits corticotomy to safely occur by drilling directly through the gingivae, the cortical plate, and into the medullary bone.

A twenty-second continuing object of the invention is to provide an apparatus and method that eliminates the need for a bone graft for a person with normal height and density of alveolar bone.

A twenty-third continuing object of the invention is to provide an apparatus and method that improves the detection of the location of the anatomical landmarks to be avoided while performing a corticotomy.

A twenty-fourth continuing object of the invention is to provide an apparatus and method that permits the detection of unusual or oddly located landmarks peculiar to a specific patient (anomalies).

A twenty-fifth continuing object of the invention is to simplify the procedure for an accelerated orthodontic procedure.

A twenty-sixth continuing object of the invention is to simplify the procedure for an accelerated orthodontic procedure sufficient to permit widespread use of such procedure by the mainstream of practicing dentists.

A twenty-seventh continuing object of the invention is to reduce apprehension for the prospective patient regarding any of the high cost, complexity, discomfort, or risks of prior art techniques to provide accelerated orthodontic procedure.

A twenty-eighth continuing object of the invention is to provide an apparatus and method that lessens damage to the gingivae during corticotomy.

A twenty-ninth continuing object of the invention is to provide an apparatus and method that is adapted to use a laser to penetrate through the gingivae and cortical plate.

A thirtieth continuing object of the invention is to provide an apparatus and method that uses 3-D imaging software to generate from a CTscan, x-ray, or other type of imaged file a positive structure of the size and shape of at least a portion of the jawbone of a patient useful in the determination of where to drill through the cortical plate.

A thirty-first continuing object of the invention is to provide an apparatus and method that that uses 3-D imaging software to generate from a CTscan, x-ray, or other type of imaged file a positive structure of the size and shape of at least a portion of the jawbone of a patient, and wherein the structure that is produced is sufficiently transparent to reveal the location of certain landmarks in the jawbone.

A thirty-second continuing object of the invention is to provide an apparatus and method that that uses 3-D imaging software to generate a positive structure of the size and shape of at least a portion of the jawbone of a patient, and wherein the structure is sufficiently transparent to reveal the location of certain landmarks in the jawbone, and wherein the structure is for use in creating a template to indicate, during corticotomy, safe interproximal regions for drilling through the gingivae and through the cortical plate.

A thirty-third continuing object of the invention is to provide an apparatus and method that uses imaging technology to provide a real-time indication to a dentist where it is safe to drill through the gingivae and through the cortical plate.

A thirty-fourth continuing object of the invention is to provide an apparatus that provide a template that is placed over at least a portion of the jawbone of a patient, and wherein the template provides depth and directional information to the dentist sufficient to permit the dentist to drill through the gingivae and cortical plate into the medullary bone while avoiding landmarks in the medullary bone.

A thirty-fifth continuing object of the invention is to reduce the risk of damage to landmarks during corticotomy.

A thirty-sixth continuing object of the invention is to provide a method and apparatus for indicating where a dentist may drill through the gingivae and through the cortical plate and which also provides means to limit the depth of drilling of each that is accomplished to an vascular area in the medullary bone.

A thirty-seventh continuing object of the invention is to provide a method for drilling through the gingivae and through the cortical plate and into a vascular region of the medullary bone and without having to rely on visual observation of the surface of the cortical plate to ensure that drilling to a sufficient depth has occurred.

Briefly, an apparatus useful for corticotomy that is constructed in accordance with the principles of the present invention includes a template that is placed over at least a portion of the teeth and gingivae of a patient. The template includes visual indication where it is safe to penetrate (i.e., to drill) through the gingivae and through the cortical plate in an interproximal region of the cortical plate between at least two adjacent teeth sufficient to penetrate into the medullary bone and to induce RAP. Modifications are described to the template that include depth regulation and directional information. Different methods of making the template are also described. Accordingly, a method for performing corticotomy without the requirement of a mucoperiosteal flap procedure is described in which drilling through the gingivae and cortical plate is accomplished while avoiding landmarks. Modification is described where use of the template is not required and whereby other real-time indications as to location for drilling are provided on the gingivae during the procedure.

BRIEF DESCRIPTION OF THE DRAWINGS

The accompanying drawings, which are incorporated in and constitute a part of this specification illustrate embodiments of the invention and, together with the description, serve to explain the features, advantages, and principles of the invention.

DETAILED DESCRIPTION OF THE PREFERRED EMBODIMENT

Referring now on occasion to all of the FIGURE drawings, the present invention provides an apparatus and a method of accomplishing an improved corticotomy facilitated orthodontic procedures. According to a preferred embodiment, a surgical template 20 (FIG. 1) is securely positioned over a patient's teeth and gums (also referred to herein as gingivae and identified by reference numeral 83, FIG. 3) and is constructed so as to indicate the regions of the gums 83 which may be safely penetrated, in numerous locations, passing then through a cortical plate and into an underlying medullary bone within a jawbone (66, FIG. 2), by a small drill or needle (102, FIG. 9) thereby effecting the corticotomy.

The use of the small drill 102 or needle 102 is referred to as a needle corticotomy. After the corticotomy is completed, the patient's cortical plate softens, as known to those familiar with the art, within typically 1 to 7 days an amount sufficient to begin moving the teeth in an accelerated manner by means of the application of light forces using any of the currently available conventional orthodontic techniques. Future devices to assist the movement of teeth may also be developed and used in conjunction with the instant invention.

The cortical bone remains soft for a period of time, thereby permitting faster movement of the teeth in response to light forces that are applied to them to urge them in the desired direction.

Figure 1:
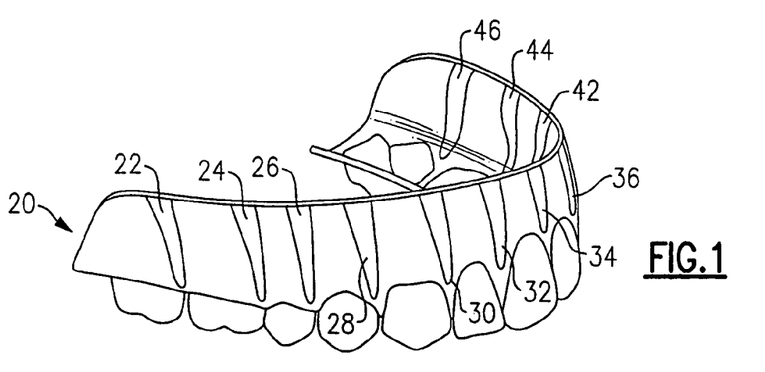
FIG. 1 is a perspective view of an embodiment of the surgical template apparatus in accordance with this invention with markings indicating the regions suitable for penetration of the gingivae and subsequently the underlying cortical plate.

Continuing now to refer in greater detail to the various FIGURES wherein like reference characters refer to like parts, there is shown at 20 in FIG. 1, the surgical template constructed in accordance with the subject invention.

An accelerated orthodontic procedure is facilitated by performing a corticotomy involving the perforation of a patient's cortical plate. A detailed description of a corticotomy, in general, is not included herein other than to describe the differences thereto that arise from use of the instant invention as it relates to a needle corticotomy because corticotomies are generally well known to those having ordinary skill in the dental arts.

Figure 2:
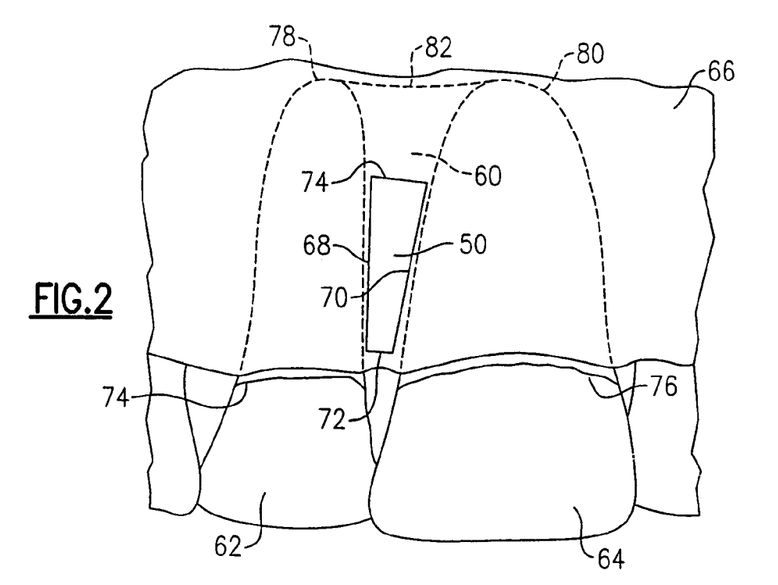
FIG. 2 is an upper anterior view of the cortical regions showing the spatial relationship between the triangle region and the surrounding anatomical features of a patient.

Referring momentarily to FIG. 2, the jawbone 66 includes at the surface the cortical plate which includes a thickness that varies patient to patient, as described in greater detail hereinafter. Covering the cortical plate are the gingivae 83 or gums. Protruding from the cortical plate are the various teeth (62, 64 FIG. 2).

Figure 3:
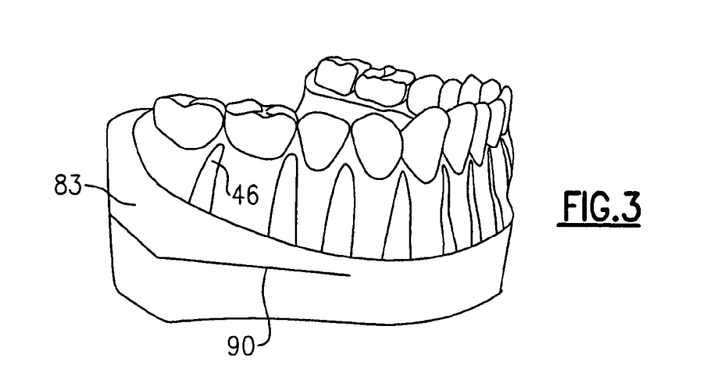
FIG. 3 is a right buccal view of a lower or mandibular model of a jaw with the cortical regions projected on the surface of the mucogingival model revealing the underlying landmark features and anatomy of a patient.

Underneath the cortical plate is the medullary bone where each tooth's 62, 64 root 68, 70, FIG. 2, are disposed. The medullary bone contains any of a variety of landmarks (one landmark is shown in FIG. 3, reference numeral 90) that are to be avoided. The various landmarks to avoid are well known to those having ordinary skill in the dental arts. Serious harm to the patient can occur if certain of these landmarks are contacted during the corticotomy.

A primary advantage, as is described in greater detail hereinafter, is that the instant invention permits the desired corticotomy to occur without the removal of the mucogingival tissue 83. The improved needle corticotomy is accomplished by penetrating the mucosal tissue (gums 83) and the underlying cortical plate at very specific locations and in very specific directions as indicated by the surgical template 20. The template 20 is custom made (molded) to precisely fit each patient and is positioned over the teeth 62, 64 and gums 83 after the landmarks (to avoid) have first been identified, as described in greater detail hereinafter, and factored into design of the template 20.

FIG. 1 provides an overall perspective view of the surgical template 20, showing its major features and their spatial relationships.

Further referring to FIG. 1, the surgical template 20 is so engineered to present targeted areas through which penetrations using the needle 102 or drill 102 or by other means, as described in greater detail hereinafter, may be made with assurance that the key anatomical landmarks will be avoided. These preferred areas are used to guide the dentist as he or she drills through the patient's gingivae 83 and also through the patient's cortical plate beneath the gingivae 83. These areas are exemplified by a plurality of regions 22, 24, 26, 28, 30, 32, 34, 36, 38, 40, 42, 44, and 46.

These regions 22-46 are of any preferred or desired size and shape and they will vary from patient to patient, depending on the general or unique location of the landmarks. Often, the regions 22-46 will have a common shape that resembles either a triangle or a "tall" type of a trapezoid. However, depending on the unique landmarks that a particular patient may have, the shape of any of the regions 22-46 will vary, as desired. Some of the regions 22-46 may resemble a square or a rectangular, whereas some may be more oval or circular, or include any conceivable type of a polygonal shape. The shape of any one region 22-46 may vary significantly from the shape of any adjoining region.

The regions 22-46 are included on the surgical template 20 in two basic ways. There is a third way to indicate the regions, discussed in greater detail hereinafter, which does not utilize the template 20 or any variation thereto.

Each patient differs anatomically and therefore the surgical template 20 is constructed specifically to correspond to the unique anatomical features of each patient. The surgical template 20 is generally comprised of a molded element that closely follows the contours of the patient's teeth 62, 64 (and other teeth) and gingival 83 regions proximal to the teeth 62, 64 that are to be repositioned.

The surgical template 20 is made to "form-fit" to the patient's specific anatomy. As shown throughout the drawings, the template 20 extends the length of either the upper or lower jawbone 66. This is generally preferred to ensure that a firmer or better fit occurs. However, if preferred, a smaller, shorter, or other specific section of the template 20 can be used when only one or two teeth are to be repositioned and a more localized corticotomy is required. It is also important to note that the template 20 is preferably saved even after the corticotomy is performed.

The needle corticotomy is intended to soften the cortical plate proximate areas of injury to the plate by producing regional acceleratory phenomena or RAP, as is discussed further hereinafter. If, however, it is determined that after having performed a needle corticotomy, as described herein, there is insufficient RAP occurring, the template 20 may be reused and a repeat needle corticotomy accomplished at any site (i.e., at any particular region 22-44) where RAP has slowed down after 90-120 days. Therefore, the template 20 is saved for possible future use.

The preferred method of constructing the surgical template 20 is the use of CAD/CAM technology which consists of a CTscan to create an image file. The image file is used to create a virtual 3D model of each (upper and lower) jawbone 66 depicting also all of the teeth 62, 64, roots 68, 70, critical landmarks 90 and cortical regions 22-46 over an interproximal bone 60 (FIG. 2). Computer software is used for this purpose and is known. The surgical template 20 is then virtually created to fit a virtual model of the jawbone 60. This information is stored on a CD-ROM and is then used to create an actual physical model of each jaw and then an actual physical surgical template (i.e., a variation in construction that is still used as the template 20) is created to fit each jaw, which includes each physical model made from the image file as well as each of the patient's actual jawbones 66. The actual physical model of each jaw is preferably created using a clear plastic type of outer material with landmarks shown in color within the model. That makes it easy, when constructing the template 20, to create the regions 22-46 that avoid the landmarks. As is described in greater detail hereinafter, an effective way to produce the physical models is by the use of stereo-lithography.

One possible way to create the surgical template 20 is for the dentist to take an impression (well known) of the patient's teeth 62, 64 and gums 83 and then construct a plaster model (not shown) from the impression. The plaster model is then used to form the surgical template 20 over the plaster model using a thermo-suction technique (well known).

It is also known how to construct a virtual model of a jaw and then a physical model using the CTscan image file. This practice has been used when an implant, used to replace a missing tooth, is implanted into a jaw and the dentist must drill down from the top of the jaw. The software to generate the preferred view of the jawbone used for the invention as described herein is obtained by modification to the software.

There are other well known techniques and methods that can readily be adapted to create the desired template 20. For example, vacuum thermoforming techniques using an Essix Brand Vacuum Machine (at the worldwide web at essix.com) can also be used to form the template 20 over a model of the jawbone 66. A plastic sheet is thermoformed onto a plaster model of the patient's gums and teeth, thereby providing a base to be used to create the actual finished template 20. Landmarks are located by x-ray or CTscan and are then superimposed on the template base.

It is not necessary to indicate the location of the landmarks on the template 20, however, they can be included, if desired. It is, however, necessary to assist the dentist in providing areas that are safe to drill into which will avoid these landmarks. While including all of the landmarks on the template 20 and allowing the dentist to drill around them is possible, it is not preferred.

Rather, it is preferred that the regions 22-46 be included on the template 20 that reveal areas that are "safe" to penetrate through the gingivae 83, through the cortical plate, and into the vascular regions of medullary bone underneath. In other words, it is preferred to show the dentist areas where it is safe to drill rather than to show areas to avoid drilling. It also improves safety by showing the safe regions 22-46 because those areas that are shown as safe to drill into on the template 20, that is the regions 22-46, include a safety margin that helps ensure that the dentist will stay sufficiently far away from key landmark areas, for example, from roots, nerves, vessels, sinus areas, etc.

The template 20 is preferably constructed of a sheet of transparent plastic to allow viewing of the teeth 62, 64 and gums 83 over which it is applied; however, other moldable materials may also be suitable. The material used to form the template 20 is preferably of sufficient thickness and rigidity so as to maintain its form when it is applied over the teeth 62, 64 and gums 83. According to a modification, described further hereinafter, the thickness becomes a variable.

Continuing to refer now in particular to FIG. 2 is shown, amongst other elements, the typical anatomical features of a patient. Regions of the cortical plate determined to be safe to penetrate are determined and are projected to the surgical template as the regions 22-46 in the template 20.

It is to be understood that not every tooth is necessarily repositioned during any orthodontic procedure and that therefore, not all of the regions 22-46 will always be utilized during corticotomy. In general, if a tooth is to be urged in any given direction as part of the orthodontic procedure, the needle corticotomy is performed minimally on the side of the tooth in the interproximal bone 60 where migration of the tooth is desired. However, the needle corticotomy is preferably performed on both sides of the tooth that is to be repositioned.

Additionally as mentioned earlier, the regions 22-46 are presented in either of three ways. Two of those ways are used with the template 20; a third way is described as a modification hereinafter. A preferred way is to provide a cut-out of the region where corticotomy is to occur. The dentist performing the orthodontic procedure determines this. Needle corticotomy may occur between many, most, all or only a few of the teeth. Only select regions 22-46, where the corticotomy is to occur, will appear on the template 20. This is to avoid confusion and the possibility that excess corticotomy could occur between teeth that do not require RAP.

In some cases the same dentist performing the orthodontic procedure will also perform the corticotomy, as described herein. This, of itself, is an improvement over the prior art wherein when practicing corticotomy with the prior art a more skilled practitioner, one who was able to perform the mucoperiosteal flap procedure, was required to perform the corticotomy. This procedure was more daunting and complex than many dentists would care to engage in. The instant invention allows those dentists who would not feel sufficiently skilled to perform a mucoperiosteal flap procedure to accomplish the type of needle corticotomy disclosed herein.

According to a preferred way of indicating the regions 22-46 on the template 20, each region 22-46 where corticotomy is to occur is cut out or removed to provide an opening or plurality of openings through the template 20, exposing the gingivae 83 directly underneath. As described in greater detail hereinafter, the dentist would simply use each cut-out region 22-46 to drill a plurality of holes through the gingivae 83, cortical plate, and down into the medullary bone.

According to a preferred way of indicating the regions 22-46 on the template 20, each region 22-46 where corticotomy is to occur is outlined on the template. The dentist would similarly use each region 22-46 to drill a plurality of holes that first pass through the template 20 itself ensuring that each of those holes occurs within one of the outlined regions 22-46. After puncturing the template 20, the dentist would continue drilling through the gingivae 83, cortical plate, and down into the medullary bone.

FIG. 2 shows a safe area 50 between the roots of two teeth 62, 64 that includes a generally trapezoidal overall shape. It also tends to resemble a triangular in shape as well. The safe area 50 as determined to exist between any two of the adjacent teeth 62, 64 is used to define each of the regions 22-46 that appear on the template 20.

The safe area 50, once determined, is projected onto the surgical template 20. The safe area 50 is generally defined by outlining the interproximal bone 60 between the adjacent teeth 62 and 64 as viewed from the buccal or labial view of the jaw bone 66. The safe area 50 is further defined by the surfaces of the roots 68 and 70 of adjacent teeth 62 and 64 on the sides, an upper apex 72 of the cortical triangle being defined by the gingival crest of the bone and a lower delineation 74 being preferably defined by a line drawn from a point approximately ¾ the distance of the root length of one tooth to a similar point on the adjacent tooth as measured from the base of a crown 74 and 76 where the root begins towards the apical end of the root 78 and 80. If anatomical features to be avoided are determined to lie within the safe area 50, the boundaries of the safe area 50 are adjusted to exclude those features and the adjusted safe area 50 is then projected onto the template 20 where it is either outlined (to drill through the template 20 and through the gingivae 83, cortical plate, and to the medullary bone) or the projected safe area 50 is cut out and removed from the template thereby allowing the dentist to drill directly into the gingivae 83 and continue through the cortical plate and into the medullary bone.

Experiments have shown that limiting corticotomies to the safe areas 50 (i.e., the regions 22-46) is sufficient to produce adequate softening of the cortical plate to permit accelerated tooth repositioning (RAP). The total number of guide regions 22-46 in the template 20 will be determined on a case by case basis as required to soften the appropriate interproximal cortical plate bone regions.

As in FIG. 2, the lower delineation 74 may alternatively be defined by a line 82 drawn from the apex of the root of one tooth 78 to the apex of the adjacent root 80; however, landmark features, which tend to be more prevalent closer to the root apex, such as nerves maybe located in this region and care must be taken to avoid these structures. Other potential complications of placement of the lower delineation 74 as defined from adjacent root apexes have been observed such as an increased difficulty in penetrating the more delicate mucogingival tissues 83 residing over the apical end of the root as the tissue itself tends to wrap around the drill 102 during penetration.

The use of the well fitting surgical template 20 with a closed border approximately ⅛" beyond the safe area 50 helps to prevent wrapping of the delicate mucogingival tissue in the apical area. Further, a thicker, harder plastic material, if used to create the template 20 provides an added benefit. The template 20 also holds the mucogingival tissue even firmer, which further protects the tissue from wrapping around the drill 102.

Another solution to minimize the wrapping of the delicate mucoperiosteal tissue, aside from drilling through the template 20, is to limit the size of the regions 22-46 that have been cut out to a minimal amount. This is done by creating holes within the borders of the safe areas 50 instead of a complete cut out of the plastic surface of the surgical template 20 over the safe area 50, which is also the border of the underlying interproximal bone.

This design approach provides a preferred method for providing access to the dentist when penetrating the gingivae 83 and cortical plate of bone, first, because it holds the mucoperiosteal tissue 83 more firmly which limits the wrapping effect, and secondly, because the holes that are to be drilled through the template can be color coded which provides the operating dentist with a depth guide.

The depth guide referred to here is particularly useful when a transparent virtual or physical model of the jaw is provided to the dentist, along with the surgical template or guide, since the 3D imaging software allows the software technician (who creates the virtual and actual physical models of the patient's jaw) to measure the depth of the mucosal tissue as well as the depth of the cortical plate of bone the dentist is penetrating to reach the vascular medullary bone beneath the cortical plate of bone.

Referring to FIG. 3, showing a right buccal view of the regions 22-46 (46 being identified) are projected onto the surface of the working model. The landmark anatomical features such as a mandibular canal 90 are thereby avoided. The projected safe areas 50 form the regions 22-46 and those regions where corticotomy is to occur are then cut out (or, alternately, outlined on) from the surgical template 20, thus forming the openings (or, alternately, the outlined areas) through which penetrations can safely be made without the need for mucoperiosteal flap procedure.

Figure 4:
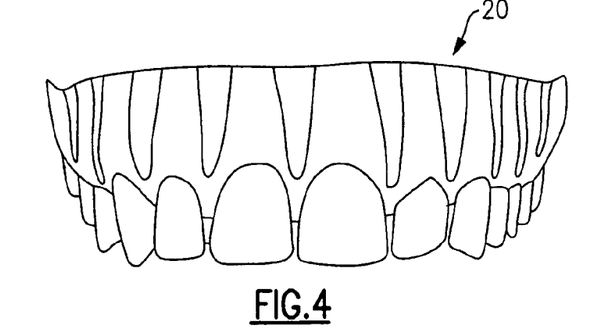
FIG. 4 is frontal view of the surgical template showing the cortical region openings.
Figures 5, 6, 10:
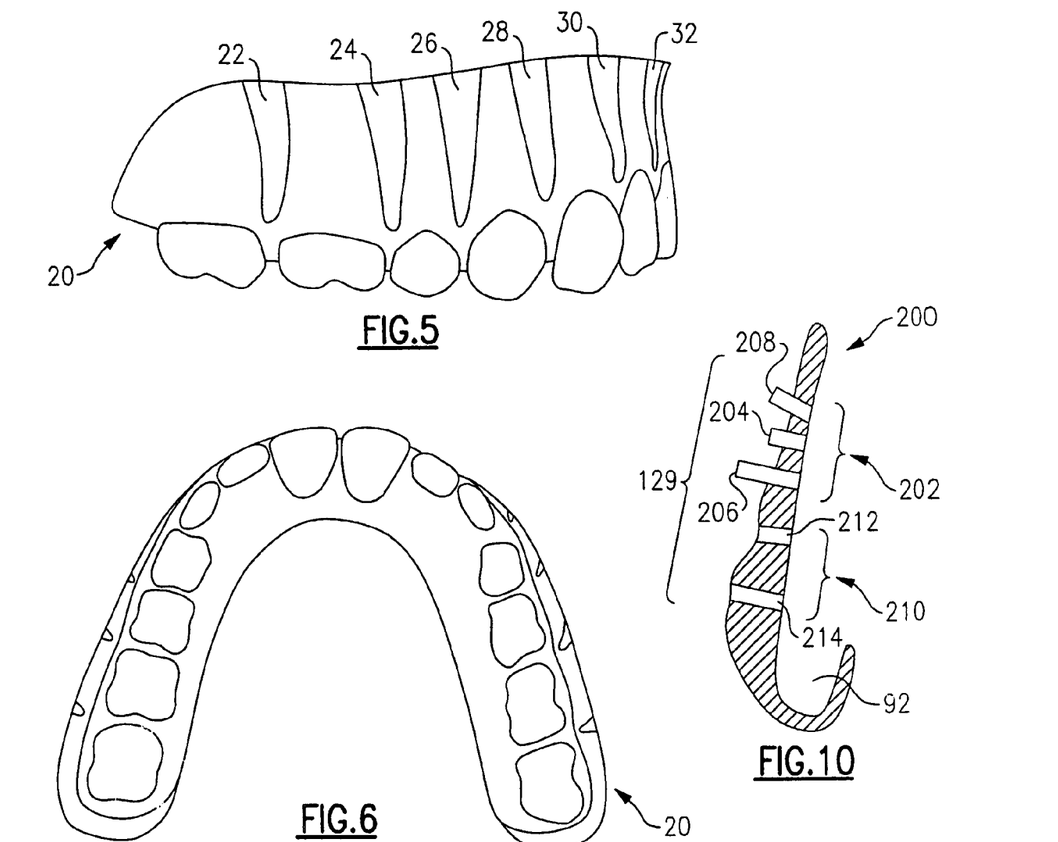
FIG. 5 is a right buccal view of the surgical template.
FIG. 6 is an occlusal view of the surgical template.
FIG. 10 is a cross-sectional view of a modified template showing alternate ways of controlling depth and hole placement and angle of penetration.

FIG. 4 shows a frontal view, FIG. 5, a right buccal view, and FIG. 6, an occlusal view of the surgical template 20 illustrate the close form fitting construction of the template to the patient's anatomy and provide alternate views of the cut out regions. Forming the plastic template 20 tightly around the teeth and gingivae 83 allows the template 20 to be held in place and in the correct position on the patient. The exact dimensions of the template 20 and the cut out regions will, of course vary, depending upon the specific anatomy of the patient.

Also, and as mentioned earlier, for certain situations where the needle corticotomy is to be performed at only a few locations, a smaller section of the template 20 (i.e., not including all of the teeth) may be provided, if preferred. If a smaller section of the template 20 is used, it must nevertheless include a sufficient number of teeth or other anatomical features of the patient so as to ensure that the smaller section is properly aligned in the patient's mouth. The smaller section, as well as the full template 20 cannot be allowed to excessively move or shift in its position while it is affixed over the patient's teeth 62, 64 and gums 83. This is because it is important to maintain the few regions 22-46 (i.e., those few that are included in the smaller section of the template 20) in their proper position over the interproximal bone 60 and away from all of the landmarks 90 it is desirable to avoid.

It is also noted that more than one template 20 can be used. For example, a first version of the template 20 (or a first section of the template 20) may be used to assist in performing a needle corticotomy with the upper jawbone (i.e., Maxillary). The first version of the template 20 would then provide a Maxillary version of the surgical template 20. A second, different version of the template 20 (or a second section of the template 20) may be used to assist in performing a needle corticotomy with the lower jawbone (i.e., Mandibular). The different version of the template 20 would then provide a Mandibular version of the surgical template 20. This is useful when teeth are to be repositioned in both the upper and lower jaws.

It is also possible to use a first section of the template 20 on one side of either the upper or lower jawbone and to simultaneously use a second section of the template 20 on another side or location of the either the same upper or lower jawbone. This is when one or two teeth are to be repositioned on the same jawbone but when these teeth are sufficiently separated from each other. The use of two sections of the template 20, as described, may be used in this situation although it is still preferred to use one continuous version of the template 20, as shown. These options are discussed herein to illustrate a few of the variations in the apparatus and method that are possible for those skilled in the art.

When the teeth of any particular patient are deemed to be especially crowded, the dentist may elect to cut the template 20 (either the Mandibular or the Maxillary versions thereof) into two or three sections to permit easier placement of the sections of the template 20 over the crowded teeth.

Figure 7:
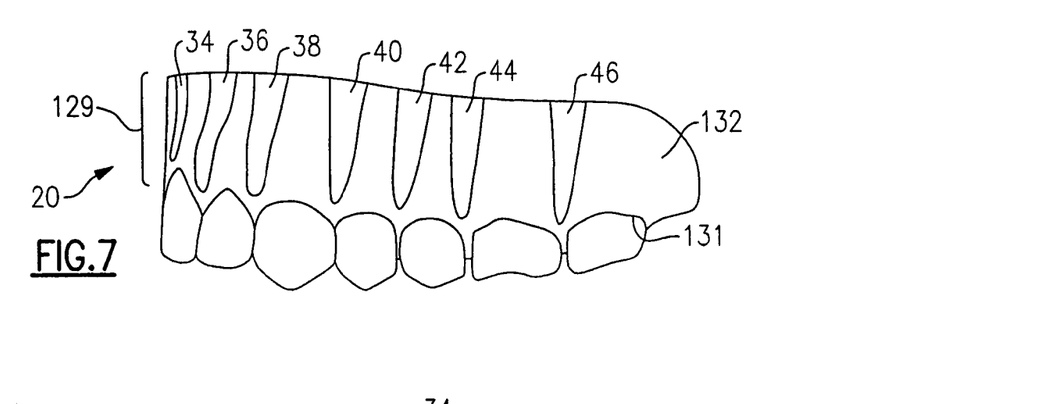
FIG. 7 is a left buccal view of the surgical template.

Referring now to FIG. 7, a left buccal view of the surgical template 20, a gingival portion of the template is indicated by bracket 129. The gingival portion 129 is that section of the template 20 that rises above the gum line or gingival crest on the Maxillary or upper version of the template 20 and which covers the gingivae 83 that are disposed over the cortical plate in the area of interest, namely where the needle corticotomy is to be performed. The gum line is indicated by marker 131. The gingival portion 129, of course, extends down from the marker 131 on the Mandibular or lower version of the template 20. The gingival portion 129 may also be generally referred to as a mucogingival or as a mucoperiosteal portion of the template 20. A mucosal extension 132 optionally protrudes from one or both ends of the gingival portion 129 of the template 20.

Figure 8:
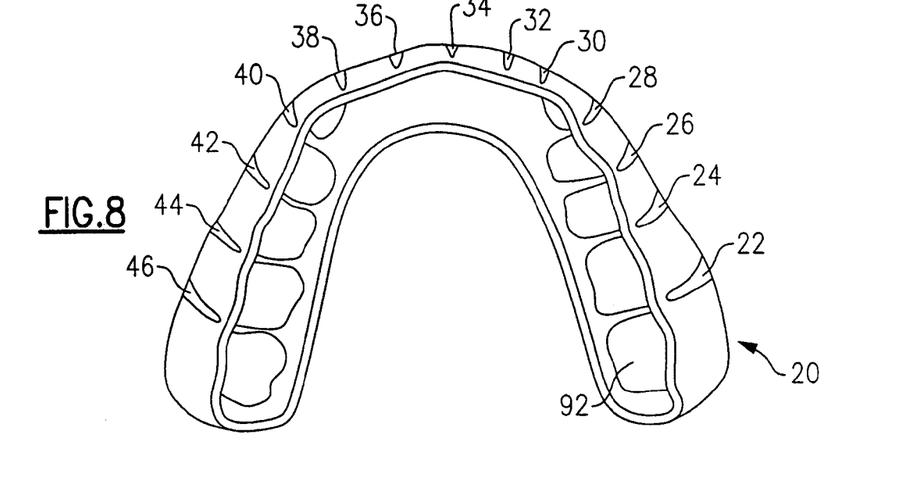
FIG. 8 is an internal view of the surgical template of FIG. 7 as seen from above.

Referring now to FIG. 8, an internal view of a surgical template 20, shows the plurality of indentations around the teeth. These indentations are the spaces into which each respective tooth fits. Such a space is exemplified by reference numeral 92. It is important to understand that the template 20 is thermoformed (or otherwise produced) so as to provide a plurality of the spaces 92 that conform well to the shape, location, and volume of each tooth. Accordingly, the template 20 fits over the teeth and gums with precision and it is retained in place by the precision of its fit.

The surgical guide (i.e., the template 20) thereby indicates the areas into which penetrations of the gingivae may be made without injuring sensitive, predetermined landmark features.

Figure 9:
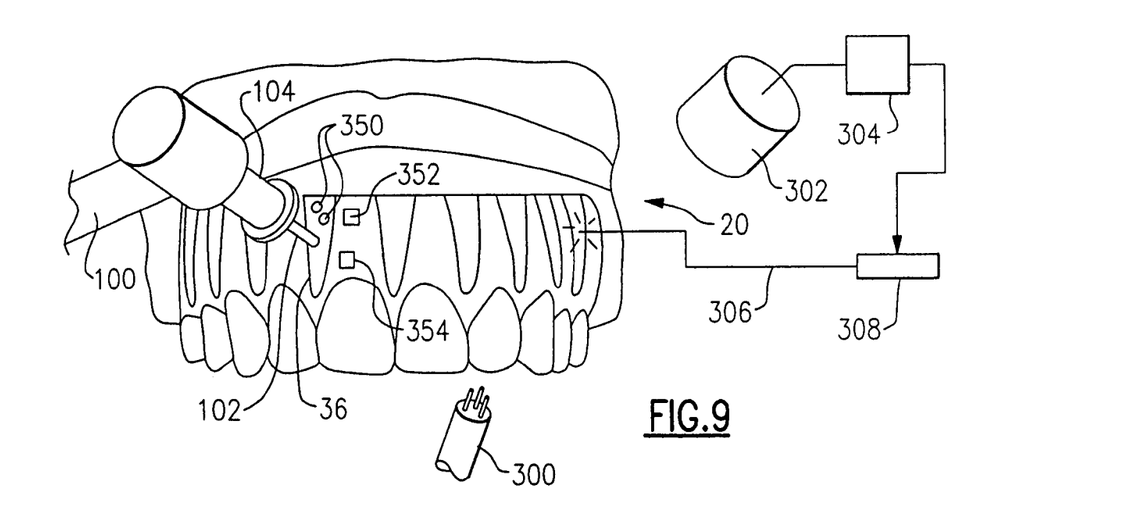
FIG. 9 is a frontal view of the surgical template in position with an X-tip needle perforating the gingivae and underlying cortical plate of bone through a cortical region that has been projected to a cut out region in the template.

FIG. 9 shows a frontal view of a Maxillary version of the template 20 in position disposed precisely over a patient's teeth and gums. Assuming that needle corticotomy is to be performed at region 36 (as shown in FIG. 9; the region numbers may change with each version of the template 20), it is preferred that a plurality of penetrations (i.e., holes that are drilled) occur at region 36 and also at each remaining region wherever corticotomy is to occur. This may include only one or two of the total number of regions 22-46 or it may extend up to and including all of the regions 22-46. Again, this is determined on a case by case basis.

The reason a plurality of penetrations is preferred to just one penetration at any given region (i.e., region 36) is because it is highly desirable to enter into a vascular region of the medullary bone and cause it to bleed. When bleeding of the medullary bone occurs, conditions for generating RAP are optimized.

In particular, the cortical plate of bone is avascular. By penetrating into the medullary bone, a blood supply is provided to the cortical plate. Osteoblasts are then sent to the cortical plate in sufficiently larger numbers which results in RAP or "regional acceleratory phenomenom" and allows the teeth to move (reposition) faster when orthodontic forces are subsequently applied.

Therefore, a plurality of penetrations, spaced 3-4 mm apart, are accomplished through the gingivae 83, through the cortical plate, and into the medullary bone underneath the region 36 to adequately soften the interproximal bone.

Also, it is possible to observe bleeding and conclude, with a high degree of accuracy, that it is originating in the medullary bone.

A number of penetrations are next made into and through the gingivae 83 that is exposed in the region 36. In general, each penetration is made as close to perpendicular with respect to the surface of the gingivae 83 as is possible. According to a preferred embodiment, the gingivae 83 that is to be punctured is exposed by the cut out area (i.e., the region 36) in the surgical template 20.

While variation is possible, a preferred way to make the punctures is by using a small diameter needle-like instrument, for example a product marketed as an X-Tip® 104 and as shown in FIG. 9, or #2 small round bur, or similar drill. The X-Tip® 104 is shown mounted in a slow dental handpiece 100 and in the preferred position (i.e., perpendicular to surface) to perform a penetration though the gingivae and through the underlying cortical plate, passing beyond the cortical plate and in to the underlying inner or medullary bone.

The cortical plate usually is from 1 mm to 2 mm thick and typically requires a 4 mm long needle or drill shaft 102 to penetrate through the gingivae 83, cortical plate, and sufficiently far into the medullary bone. When portions of the cortical plate are determined to be harder or thicker than that suitable for penetration by an X-Tip®, experiments have shown that a small round burr or other type drill is indicated and may, of course, be substituted therefore.

The needle or drill, as mentioned above, is generally inserted perpendicular through the gingivae 83 into the underlying cortical plate and subsequently into the underlying medullary bone. Experiments have shown best results when penetrations are made at approximately 3-4 mm spaced-apart distances within the region 36 and when the penetrations occur in sufficient number within the surgical template 20 cut out region 36 to maximize the occurrence of PAP and the associated softening of the cortical plate.

Softening of the cortical plate shortly after the needle corticotomy is performed requires about one week to reach the level of regional acceleratory phenomena or RAP, which as mentioned hereinbefore results in the rapid softening of the cortical plate thereby allowing accelerated repositioning of the teeth using orthodontic appliances such as braces or the aligners sold under the tradename, Invisalign®.

Experiments have further shown that after a needle corticotomy, softening of the cortical plate is sustained for approximately 90 to 120 days before re-hardening begins to secure the teeth in their new positions. It is noted that a slight pressure is maintained on the cortical plate during at least a portion of this period of time by the orthodontic appliances that are used. It is, of course, possible that re-hardening might occur sooner in the absence of these sustained slight forces by the teeth themselves.

It is possible, also, for re-hardening to occur sooner than desired, even when slight pressure is applied to the cortical plate by the teeth. If the cortical plate re-hardens before the orthodontic procedure is completed, the surgical template 20 or a section of the template 20 can be positioned again over the affected teeth that require additional movement and for the needle corticotomy to again be performed in the areas (i.e., regions 22-46) that require it.

An advantage provided by the instant apparatus and method is that the need for post-operative dressing or treatment is either greatly lessened or entirely eliminated after the minor surgical procedure (i.e., puncturing of the gingivae 83) has been completed. The usual pain and antibiotic medications used for other common types of dental procedures is usually sufficient to give the patient comfort and protection from infection.

By way of contrast, the prior art method using a mucoperiosteal full flap surgery, however, is much more invasive and the potential for infection far greater.

There are two ways to determine the depth of drilling that is required and they are either by approximation or by some form of measurement. As described above, the template 20 shows where to drill but it does not show how deep. Neither does it show how many holes to drill in any given region 22-46. The practitioner uses his skill to make such determination and this is generally a very acceptable approach. It is important to note that the regions 22-46 have already excluded the landmarks that are to be avoided so a slight variation in angle (away from perpendicular) or depth is of little concern.

It is possible to use the image file (described hereinabove) to more precisely define both the number of penetrations that are to occur in any given region as well as the depth of each penetration, separate and distinct from the next penetration.

Before a discussion of this occurs, the following description is useful in explaining how the detailed image files, useful in creating the template 20 or any variation thereto, are obtained.

The interproximal bone 60 regions that are safe to penetrate are identified by various means, for example by x-rays, MRI, ultra-sound, CT (or CAT) scans or other currently recognized diagnostic techniques as well as by future diagnostic techniques for visualizing or locating anatomical landmark features to be avoided during penetration of the cortical plate.

The preferred method of creating and manufacturing a surgical guide for use in the present invention is as follows: A CT scan is taken of the patient's upper and lower jawbones and teeth. The scan is formatted and using 3D CAD/CAM software, a virtual model of each of the jawbones is created virtually showing the jawbone in transparent plastic with a gingival layer, teeth, roots and critical landmarks visible to the end user. The gingival layer, teeth, roots and critical landmarks are preferably delineated within the transparent plastic sufficient to be readily observed. The interproximal bone 60 between all of the roots is also visible.

A safe area 50 is then drawn on the virtual model over each interproximal bony 60 area between any two adjacent teeth 62, 64 where corticotomy is to occur. Using 3D software to create a virtual model of each jawbone allows for the creation of different views to optimally display the density and depth of the cortical plate, thereby allowing "virtual holes" (penetrations) of varying circumference and depth to be placed through the gingivae and cortical plate in all of the intended interproximal bone 60 areas of the jawbones. The location of the virtual holes is in conjunction with those interproximal bony 60 areas adjacent to teeth 62, 64 that are misaligned and are in need of orthodontic movement. It is also possible to determine an ideal "virtual depth" for each penetration.

Based on the depth necessary for the end user to penetrate the cortical plate, each virtual hole is color coded to indicate the preferred depth that the drill must penetrate to optimally penetrate the cortical plate into the medullary bone. The selection of color codes is determined by number of millimeters the X-tip® or #2 round bur or other drill must be driven to penetrate the cortical plate. For instance, 2 mm length holes could be green, 4 mm holes could be yellow and 6 mm holes could be red. A file of this information is then saved and stored on a CD-ROM for use in the physical construction of the models and surgical guides (i.e., template 20).

The most accurate and cost effective method for creating a large volume of surgical template 20 guides for end users is by the process of stereo-lithography. Using the CD-ROM file (of course the CD-ROM file could be stored otherwise and emailed, for example), an actual physical model of each jawbone is manufactured, which includes all of the before mentioned features and qualities of the virtual models. The full scale model is constructed of transparent material allowing a 3D visualization of the patients' anatomy. A surgical template 20 is then constructed to fit each physical model of each jawbone.

Each of the safe areas 50 are then projected onto the surgical template 20 and included as one of the regions 22-46. As mentioned earlier, any one of the regions 22-46 may include any particular shape although a generally triangular shape (or trapezoidal) is most common.

Depending on the preference of the end user practitioner, holes of varying depths and colors are made through the surgical template. In other words, each of the plurality of individual holes that are to be drilled in any or every particular region 22-46 is pre-drilled through the template 20. After the practitioner places the template 20 over the patient, he or she simply holds the drill 102 perpendicular and drills through each of the pre-drilled holes in the template 20 that have been provided in each region 22-46. An advantage of pre-drilling the holes in the template during its manufacture (as opposed to providing the larger cut-out region) is that the gingival portion 129 provides greater support for the gingivae 83 virtually elimination the possibility that the gingivae 83 will wrap around the drill 102.

However, as previously described, if the end user prefers, a complete cut-out of each particular region 22-46 is alternately made in the template 20 thereby allowing the end user to choose the locations for penetrating the cortical plate.

Another alternate method to produce the template 20 is to take digital x-rays of the patients' teeth and jawbones in the regions where the teeth are to be repositioned. The x-rays are scaled to full size in a computer graphics program such as Microsoft Photodraw®. The anatomical landmarks are identified on the x-rays and the safe areas 50, used to define the regions 22-46, are defined and included.

A template element (the basic template sheet that conforms to the patient's anatomy, prior to its completion) is constructed using a simple vacuum thermoforming machine to suction a moldable plastic sheet (readily moldable at temperature) over a plaster model of the jawbone which the dentist makes from simple impressions of the patients' teeth and gums that he or she has taken.

Another example of a prior art type of device that can be modified for use to create the template are bleach trays, currently used to house a solution of bleach used to whiten teeth. Of course additional modifications to the trays, consistent with the disclosure herein, must be first accomplished.

The safe areas 50 where corticotomy is required are then projected onto the template element by placing the x-ray images over the template element. The regions 22-46 are then mapped and marked on the template element to indicate the cut-out regions. The regions 2-46 are then cut-out (i.e., removed) from the template element to produce the actual template 20. The cut-out regions 22-46 thus reveal the safe areas 50 for needle or drill penetration to occur.

Holes, as mentioned hereinbefore, can alternately be drilled through the surgical template 20 during its manufacture if the end user prefers this method over a full cut out. Although not preferred it is possible, as also mentioned hereinbefore, to simply outline the regions 22-46 on the template 20 and to allow the dental practitioner to drill, at the time of corticotomy, first through the template 20 and then through the gingivae 83, cortical plate, and into the medullary bone.

The template 20 is complete when it has been created to fit at least a portion of the jawbone of the patient and when it also includes some indication as to where the safe areas 50 are located for performing a needle corticotomy directly through the gingivae 50. That indication, as described herein, may include providing an outline of each region 22-46, a cut-out (i.e., removed portion from the template 20) of each region 22-46, or predrilled holes in the template 20 within each region 22-46.

As indicated, identification of the cortical safe areas 50, which are the delineated areas of interproximal bone between each tooth 62 and the adjacent tooth 64, and then the accurate projection of these safe areas 50 as each region 22-46 to the surgical template 20 are critical to the invention.

After the needle corticotomy has been performed, preferably, an aligner (a device intended to apply orthodontic forces to reposition at least one of the teeth) or braces are applied, the patient is released, and the gingivae 83 are allowed to heal. The patient preferably returns in a few days to confirm that healing is properly occurring.

It is possible to delay the application of orthodontic forces until a later time. However, it is preferred to apply the orthodontic forces sooner rather than later. Any preferred orthodontic device is used (i.e., applied) to begin to apply a force to the teeth that require repositioning. RAP occurs in response to the needle corticotomy in the affected regions 22-46 and rapid movement of those teeth also occur in response to the force that is applied to the softened cortical plate by the teeth.

The orthodontic device and movement of the teeth are periodically monitored and the orthodontic device is adjusted or replaced with a modified orthodontic device to ensure that constant pressure is maintained and applied to the teeth to reposition them as quickly as possible. Once the teeth have reached their desired position, no additional force attempting to move them a further amount is applied to them. Orthodontic devices may then be utilized, as desired, to retain the now quickly and properly repositioned teeth in their desired position until the cortical plate re-hardens and secures the teeth in position from that time forward.

Prior to the instant invention, it has not been possible to perform a needle corticotomy safely through the gingivae 83, absent first performing a mucoperiosteal flap procedure to expose the cortical plate. The time required to perform the mucoperiosteal flap procedure, the expense associated with it, the discomfort it causes to the patient, the added risks or infection, and the fear associated with these elements are all eliminated by the instant invention. The gingivae 83 are able heal readily from the punctures associated with the needle corticotomy that occur in the regions 22-46. No suturing is typically required.

It is expected that future scientific advancement will include even further modification to the instant invention, thereby allowing the dentist to perform the needle corticotomy without the use of a surgical template and/or drills as previously described.

The use of a monitor viewing screen at the site of the operation displaying an internal view of the patients jawbones making it possible to place the drill, X-tip or even to use a laser as a boring instrument or other type of cutting device and to do so without the use of the surgical template 20, while still penetrating through the gingivae 83 and cortical plate to the inner medullary bone to provide the necessary blood supply to the cortical plate to induce RAP, or the regional acceleratory phenomenon, to occur while avoiding all landmarks.

Likewise, new and better methods of correcting orthodontic malocclusions (i.e., orthodontic devices) will be used by dentists (i.e., to reposition the teeth) and when available for use, are of course suitable for use with the instant invention after the needle corticotomy has been performed.

Therefore, any method that induces RAP combined with new orthodontic methods is included in this invention which does not require either a mucoperiosteal flap or insertion or bone grafting materials.

Referring now to FIG. 10 is shown a cross-sectional view of a modified template, identified in general by the reference numeral 200. To illustrate a first method of regulating depth and direction refer to a portion of the drawing identified by bracket 202. It is preferred, though not required, that the thickness of the modified template 200 be fairly constant if the first method is employed. It is required, however, that the thickness of the modified template 20 not exceed a minimum amount required to permit drilling of the deepest required hole. The reason for this is made apparent in the following discussion.

According to the first method, a short conduit 204 is included in the modified template 200 as and where needed within any given one or more of the regions 22-46. As and where needed, a long conduit 206 is similarly provided. The short and long conduits 204, 206 are formed of any preferred material including metal or plastic or any other preferred type of material.

The short conduit 204 cannot be shorter than the thickness of the modified template 200. This is to ensure that the deepest hole that is required to be drilled into any of the regions 22-46 will penetrate into the medullary bone the desired amount when a particular length of drill or needle is used.

Conversely, the long conduit 206 cannot be any longer than would permit the chosen needle or drill to penetrate the minimum required amount into the medullary bone.

When the first method for regulating depth is used, a particular length drill or needle is specified. The length of each conduit 204, 206 is selected at each particular drill site after analysis of the image files (i.e., the CD ROM file) or other detection means to determine the location of the landmarks to avoid. Analysis of the thickness of the cortical plate and of the medullary bone are factored in to determine the optimum depth of drilling.

The speed advantage thus obtained is apparent. The practitioner performing the needle corticotomy merely selects one length of drill or needle, inserts it into the instrument, and then proceeds in rapid succession to create all of the punctures by inserting the drill or needle into each conduit 204, 206 until drilling has penetrated the full depth allowed by each particular conduit 204, 206.

Not only is the drilling depth automatically regulated and varied for each and every puncture location, but the direction of drilling is also ensured, thereby preventing any possibility that inadvertence could cause the drill or needle to wander in an unwanted direction and possibly contact a landmark.

If it is deemed especially important to avoid a particular landmark and, nevertheless accomplish a required puncturing, an angled conduit 208 is provided in the modified template 200. The angled conduit 208 includes the desired length and is other than normal with respect to a surface of the gingivae 83.

The second method of regulating depth and direction of drilling (i.e., puncturing the gingivae 83, cortical plate, and entering into the medullary bone) is accomplished as shown by referring to a portion of the drawing identified by bracket 210. The thickness of the modified template 200 is accordingly varied to produce a similar regulation to the depth of drilling as described above.

At a first thinner location of the modified template 200, a first shorter embedded conduit 212 is included that is flush with the two opposite surfaces of the modified template 200.

Similarly, at a second thicker location of the modified template 200, a second longer embedded conduit 214 is included that is also flush with the two opposite surfaces of the modified template 200.

The dentist similarly is instructed to use a drill or needle of a particular length and to drill, in succession, through all of the embedded conduits 212, 214 in the modified template 200. Any of the embedded conduits 212, 214 may of course be angled away from normal, if desired.

With either method, it is of course possible to require a change in either the length or diameter (another variable that is regulated by the conduits 202, 204 or by the embedded conduits 212, 214) of the drill or needle, should that be necessary to accommodate anomalies in the anatomic features of the patient.

Not specifically shown, but apparent after the instant disclosure, a modification of the second method of regulating depth and direction (i.e., varying the thickness of the modified template 200) includes the omission of the embedded conduits 212, 214 from the modified template 200.

It is not generally preferred that both methods for controlling depth and direction be employed on the same region of the modified template 200, although it is possible. It is generally preferred to construct any version of the modified template 200 so that it utilizes only one, but not both, of the methods for controlling depth and direction.

It is possible, however, to construct the modified template 200 using both methods, one at certain regions 22-46 and the other at a remainder of the regions 22-46. For example, the conduits 202, 204 may irritate the tissues of the cheek farther back in the mouth and may therefore not be used toward the rear but instead proximate the front teeth, while the actual depth of the modified template 200 may be varied in these more rearward portions to lessen discomfort to the cheek.

It is important to note that the number of penetrations that are required at any one of the regions 22-46 include a sufficient number of penetrations through the cortical plate and into the medullary bone and at preferred spaced apart intervals to cause a sufficient softening of the cortical plate. While generalizations may be made, this can also vary from patient to patient.

Also shown in FIG. 9, are a few of the plurality of bore holes (i.e., punctures) 350 that have been accomplished in the region 36 where needle corticotomy is occurring.

Referring also to the side is shown a first color code 352 and below it a second color code 354 that are provided on the template 20, as desired. The first color code 352 includes a different color than the second color code 354. Each color code 352, 354 instructs the dentist to make the punctures that are proximate any given one of the color codes 352, 354 at a particular depth. The preferred depth for each hole or group of holes is determined by analysis of the anatomical features and landmarks and is optionally provided as a guide for the dentist to follow.

Another expected, common method of utilizing the instant invention is to provide the template 20 as the first template covering a full arch to allow for a full corticotomy when desired. This is to assist for general types of tooth movement, such as expansion or retraction.

A second and, as desired, a plurality of successive templates (not shown) are created at various stages of the aligners or braces where certain desired tooth movements need additional corticotomy treatment to facilitate optimally rapid tooth movement. The second and successive templates are typically created at the beginning of difficult tooth movements, such as rotations, closing large spaces, applying a torque for angulation of roots, eruption, and distalizing or mesializing of teeth.

The second and successive templates can also include a full arch, anterior arch, quadrant (i.e., half arch), or any portion of arch, as desired, depending primarily on the amount of corticotomy that is required to keep tooth movement progressing as rapidly as possible.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. A dental corticotomy system comprising;
    a dental template having
        an interior surface,
        an exterior surface,
        a first edge, a second edge generally opposite the first edge,
   the interior surface proximate to the first edge covering at least two adjacent teeth, the interior surface further configured to extend from the first edge and conform to gingivae and mucogingival tissue and to connect to the second edge, An image processing means for storing and manipulating an image file containing at least one safe area, a means for transposing the at least one safe area onto the exterior surface of the dental template whereby penetration of a cortical plate in the at least one safe area induces regional accelerated phenomenon.

2. The dental corticotomy system of claim 1 wherein the at least one safe area further comprises a means for indicating a drill depth.

3. The dental corticotomy system of claim 1 wherein a distance between the interior surface and the exterior surface defines a drill depth for the at least one safe area.

4. The dental corticotomy system of claim 1 wherein the dental template is rigid.

5. The dental corticotomy system of claim 1 wherein the at least one safe area contains at least one hole.

6. The dental corticotomy system of claim 1 wherein the at least one safe area contains at least one drill guide.

* * * * *